(12) United States Patent
Crandall (10) Patent No.: US 11,680,234 B2
(45) Date of Patent: Jun. 20, 2023

(54) PREPARED PLATED MEDIA PRODUCT

(71) Applicant: BECTON DICKINSON AND COMPANY, Franklin Lakes, NJ (US)

(72) Inventor: Ryan D. Crandall, Manchester, MD (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 98 days.

(21) Appl. No.: 17/314,098

(22) Filed: May 7, 2021

(65) Prior Publication Data
US 2021/0261895 A1 Aug. 26, 2021

Related U.S. Application Data

(62) Division of application No. 16/075,345, filed as application No. PCT/US2017/016810 on Feb. 7, 2017, now Pat. No. 11,028,354.

(Continued)

(51) Int. Cl.
*C12M 1/18* (2006.01)
*C12M 1/00* (2006.01)
(Continued)

(52) U.S. Cl.
CPC .............. *C12M 1/18* (2013.01); *C12M 23/02* (2013.01); *C12M 23/04* (2013.01); *C12M 23/10* (2013.01);
(Continued)

(58) Field of Classification Search
CPC ........ C12M 1/18; C12M 23/02; C12M 23/04; C12M 23/10; C12M 23/26; C12M 23/28;
(Continued)

(56) References Cited

U.S. PATENT DOCUMENTS 3,532,470 A 10/1970 Rochte
3,700,089 A 10/1972 Halbartschlager et al.
(Continued)

FOREIGN PATENT DOCUMENTS

CN 1918048 A 2/2007
EP 0401660 A1 12/1990
(Continued)

OTHER PUBLICATIONS

Machine Translation of JP2013183952A (Year: 2023).*
(Continued)

*Primary Examiner* — Michael L Hobbs
(74) *Attorney, Agent, or Firm* — Botos Churchill IP Law LLP (57) ABSTRACT

The present invention relates to systems and methods involving interconnected plate components, including bases, lids and covers, interconnected in a manner such that a continuous strip of each component is prepared. The continuous strips may be stored as rollstock in a reel style. The physical properties of each continuous strip allow the base, lid and/or cover to include means for positive control. In one embodiment, the continuous strip of bases is advanced and processed through an automated system with positive control, and remains in the form of a continuous strip until agar in the bases is cured, at which time the bases are singulated. When a lid is applied to a base using methods described herein, an airtight seal is formed improving the quality of culture media used in testing.

6 Claims, 5 Drawing Sheets

Related U.S. Application Data (60) Provisional application No. 62/292,503, filed on Feb. 8, 2016.

(51) Int. Cl.
*C12M 3/00* (2006.01)
*C12Q 1/02* (2006.01)
*C12M 1/22* (2006.01)
*C12M 1/12* (2006.01)

(52) U.S. Cl.
CPC ............ *C12M 23/26* (2013.01); *C12M 23/28* (2013.01); *C12M 23/38* (2013.01); *C12M 23/44* (2013.01); *C12M 23/46* (2013.01); *C12Q 1/02* (2013.01)

(58) Field of Classification Search
CPC ...... C12M 23/38; C12M 23/44; C12M 23/46; C12Q 1/02
See application file for complete search history.

(56) References Cited

U.S. PATENT DOCUMENTS

| | | |
|---|---|---|
| 6,632,653 B1 | 10/2003 | Astle |
| 7,504,252 B2 | 3/2009 | Wood |
| 2002/0102167 A1 | 8/2002 | McEntee |
| 2003/0211619 A1* | 11/2003 | Olson .............. A61B 5/150419 422/68.1 |
| 2004/0071599 A1* | 4/2004 | Rusch .............. G01N 35/00009 422/552 |
| 2004/0072339 A1 | 4/2004 | Lemonnier |
| 2004/0238380 A1 | 12/2004 | Newman |
| 2006/0035271 A1 | 2/2006 | McEntee |
| 2010/0055776 A1* | 3/2010 | Weibezahn ............ C12M 23/00 435/297.1 |
| 2011/0207169 A1 | 8/2011 | Markin |
| 2014/0220610 A1 | 8/2014 | Chandrapati et al. |

FOREIGN PATENT DOCUMENTS

| | | | |
|---|---|---|---|
| EP | 0866119 A2 | 9/1998 | |
| GB | 2036364 A | 6/1980 | |
| JP | 2004196304 A | 7/2004 | |
| JP | 2005234576 A | 9/2005 | |
| JP | 2006182364 A | 7/2006 | |
| JP | 2013183952 A * | 9/2013 | ............... A61J 7/00 |
| JP | 2013183952 A | 9/2013 | |
| WO | 9712056 A1 | 4/1997 | |
| WO | 03016175 A1 | 2/2003 | |
| WO | 03090811 A2 | 11/2003 | |
| WO | 2015169499 A1 | 11/2015 | |

OTHER PUBLICATIONS

Office Action issued in corresponding Japanese Patent Application No. 2021-115409 dated Jun. 21, 2022, (8 pp.).
The Second Office Action for Chinese Patent Application No. 201780010188X, dated Feb. 10, 2022, pp. 1-22.
Chinese First Office Action issued in CN application No. 201780010188X dated Jul. 5, 2021.
First Examination Report issued in corresponding Australian Patent Application No. 2017218430 dated Aug. 4, 2021, 6 pp.
International Search Report for Application No. PCT/US2017/016810 dated May 16, 2017.
Japanese Office Action received in 2018-560725, dated Oct. 27, 2020, pp. 8.
Supplementary Partial European Search Report issued in corresponding EP application No. EP17750626 dated Aug. 15, 2019.
Office Action issued in corresponding Japanese Patent Application No. 2021-115409 dated Jan. 5, 2023 (5 pp).

* cited by examiner

PREPARED PLATED MEDIA PRODUCT

CROSS REFERENCE TO RELATED APPLICATION

This application is a divisional of U.S. application Ser. No. 16/075,345, filed on Aug. 3, 2018, allowed, which application is a national phase entry under 35 U.S.C. § 371 of International Application No. PCT/US2017/016810, filed Feb. 7, 2017, which claims the benefit of the filing date of U.S. Provisional Patent Application No. 62/292,503, filed Feb. 8, 2016, the disclosures of which are hereby incorporated by reference herein.

BACKGROUND OF THE INVENTION

It is well known to utilize culture media, an agar, or other suitable media to provide the means for culturing and analyzing microbiological specimens. Both manual and automated means of using systems for sample growth are known in the art.

As is commonly known, use of culture media for conducting sample growth typically involves the use of a petri dish as a container. Containers are prepared and used individually. Thus, whether or not automated means are used, each container is handled separately when filled with an agar. Once filled, containers are generally stored under curing conditions held until ready to be inoculated. For example, after application of the culture medium, the container is cooled and a lid is applied for the duration of the curing process.

Once the culture medium is in condition for inoculation, any lid in place on the container is removed. Inoculation is then performed using means such as streaking to apply samples to the surface of the culture medium. The sample is then placed in an incubator. Incubation is carried out for a length of time deemed sufficient for measurable microbial growth to have occurred. This process is repeated for each individual dish.

Petri dishes present significant challenges when used in high volume, automated processes. One alternative to conventional petri dishes is the 3M™ Petrifilm™ *Salmonella* Express product. The 3M™ plates include a top film and bottom film wherein the top film is attached to the bottom film on one side of the plate and is flush with the bottom film when in a closed position. The attachment on one side allows the top film to be opened via a lip of the top film located on the side opposite from the attachment. Pulling the lip facilitates peeling of the top film from the bottom film. When this type of plate is used, the culture medium is placed onto the bottom film while the top film is held open. The top film is then rolled down over the bottom film. A spreader is then pressed onto the plate to prepare the culture medium. Once sufficient time has lapsed to prepare the culture medium, the top film is opened and the culture medium is inoculated. The film is once again rolled down and a sweeping motion is applied to the top film to remove air bubbles. The plate is then incubated until the sample is ready for analysis.

Using thermoformed culture dishes alleviates manufacturing and cost challenges. However, such systems do not solve moisture problems and irregularities in the agar during the curing process. As a result of these issues, plates can become contaminated due to the lack of an air tight seal.

Thus, there is a need for a plate system with improved efficiency when used in an automated system that can also prevent sample contamination.

BRIEF SUMMARY OF THE INVENTION

This invention relates to a system including rollstock of plate components adapted for ease of use in automated systems that facilitate injection of a base plate with an agar and inoculation of base plates with microbiological specimens, also referred to as samples.

In one aspect, the invention relates to a system of dispensable plates where the plates are used for preparing and inoculating culture media. The system includes three continuous strips of plate components. The first is a continuous strip of bases having a reservoir portion and a lip surrounding the reservoir. The second is a continuous strip of lids, each lid adapted to be placed on and attached to the lip of the base. And the third is a continuous strip of covers. Each cover includes a peripheral planar surface extending between an at least one edge of the cover and a raised portion remote from the at least one edge of the cover, the raised portion rising from the peripheral planar surface such that the raised portion includes an at least one wall extending upward from the peripheral planar surface. Each cover is adapted to be placed over the lip of the base and attached directly to the base.

The material of the base, lid and cover can be a thermoplastic. The base, lid and cover can also be adapted to advance through an automated injection and inoculation system subject to positive control. Positive control can be obtained through the inclusion of a plurality of timing features on the base, lid and cover. The lid and the base can be shaped such that both the lid and the base include four edges, where two edges of the lid are longer than the corresponding two edges of the base. The at least one wall of the raised portion of the cover can include at least one opening for ventilation.

In another aspect, the system is a roll of thermoformed plates. The roll includes a sufficient plurality of bases to be stored in a roll format. Typically, a roll constitutes at least four and up to tens or hundreds of bases. Each of the plurality of bases are connected along one common edge to an adjacent base such that plurality of bases form a linear strip of bases. The plurality of bases are adapted to wrap and fold in a spiral or otherwise reel style shape when the combined length of the plurality of bases is sufficient to do so.

The connection between bases can include a weaker portion along a line of interconnection delineating the bases. The weaker portion can be a perforation. In one embodiment, each base includes a cover heat sealed to its respective base.

In yet another aspect, the invention relates to a method of testing and analyzing samples using plated media. The method involves placing a plurality of interconnected bases adapted to provide positive control onto an automated system. The steps include processing the plurality of interconnected bases by depositing agar in at least one base therein. The next step involves attaching the least one base with a corresponding lid, and once attached, heating both. With the lid in place, the next step involves advancing and inverting the plurality of bases and lids. This is followed by subjecting the inverted bases and lids to reduced temperatures, accelerating the curing of the agar in the at least one base. Subsequent to curing, the bases to be inoculated are separated from the plurality of interconnected bases. The next step involves peeling and removing the lid from the at least one base. Once the lid is removed, the next step involves inoculating the agar with a biological sample and then securing a cover onto the at least one base, the cover serving to contain the contents of the inoculated medium. The sample is then incubated. When incubation is complete, the cover is opened to analyze the sample.

The method can also include unwinding the plurality of interconnected bases wherein each base includes timing features. When placing the plurality of interconnected bases onto an automated system, the timing features provide positive control to advance the bases, covers and lids through the system.

DETAILED DESCRIPTION

Figure 1A:
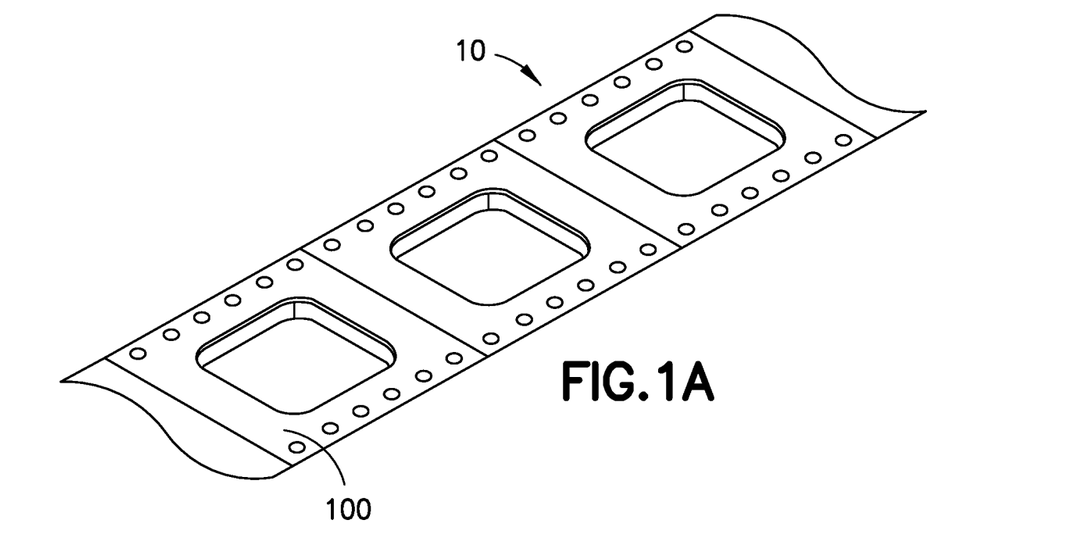
FIG. 1A represents a continuous strip of bases.
Figure 1B:
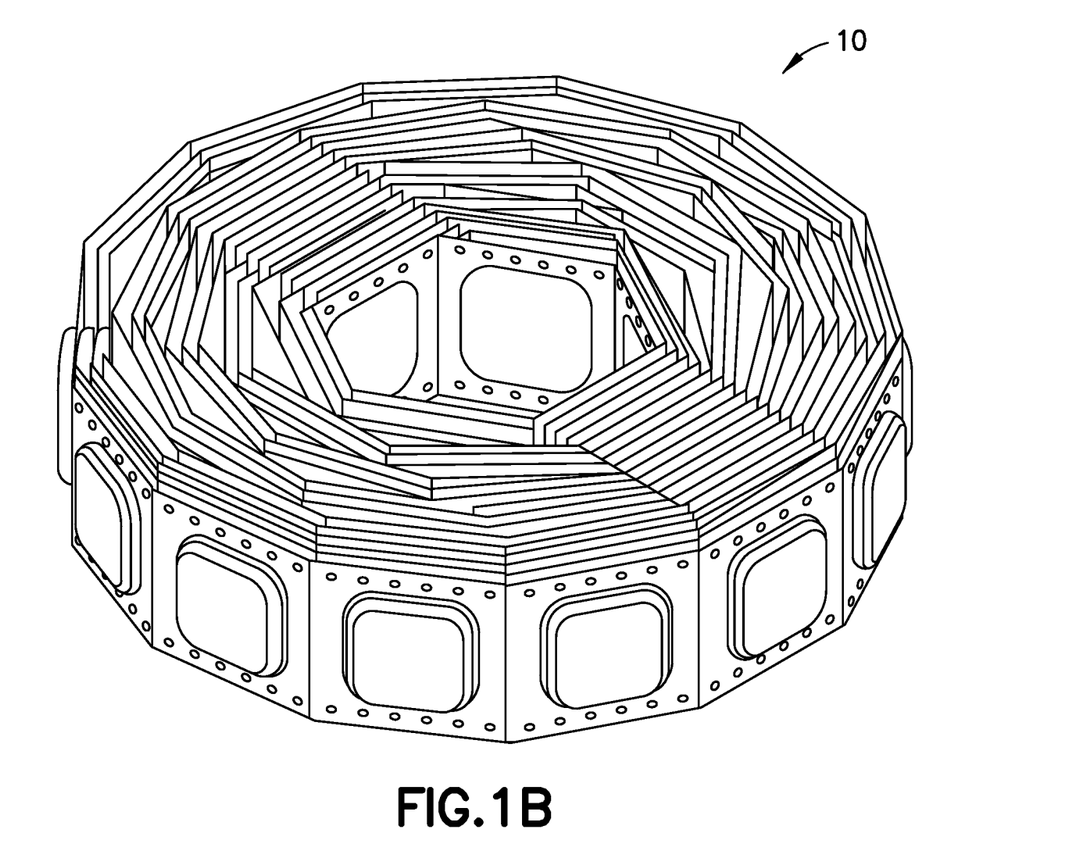
FIG. 1B represents rollstock comprised of a continuous strip of interconnected bases.
Figures 2A, 2B, 2C:
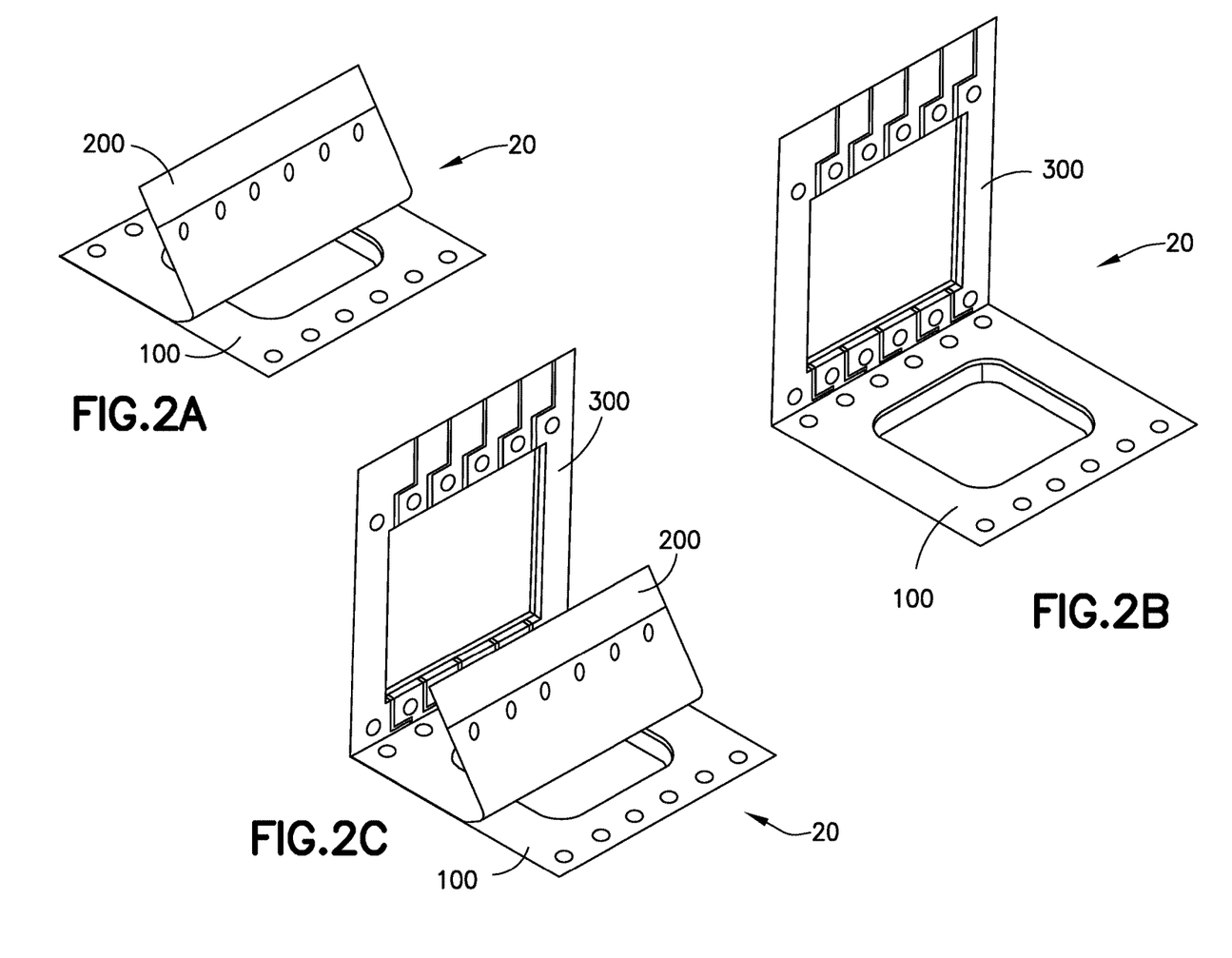
FIGS. 2A, 2B, and 2C represent an assembled plate at various stages of the testing process.

In a first embodiment of one aspect of the invention illustrated in FIG. 1A, a plurality of bases 100 are interconnected in a continuous strip 10 such that each base is connected in a linear series. FIG. 1A illustrates a continuous strip 10 although the embodiment is for purposes of illustration, and the strip can have a larger number of interconnected bases 100 than that shown in FIG. 1A. For example, many bases 100 can be linearly interconnected as rollstock, as illustrated in FIG. 1B. Other continuous strips can include a plurality of interconnected lids 200 or covers 300. As described herein and unless otherwise noted, rollstock or filling line are intended to refer to the continuous strip 10 of interconnected bases. Referring to FIGS. 2A-2C, there is illustrated a single base in the series of bases illustrated in FIG. 1A with additional layers assembled thereto. The terms base, lid and cover, hereinafter referred to individually in some cases as components, when used alone or in combination, are intended to refer generally to discrete portions of assembled plates 20 which may be used as part of an automated system for testing samples as described herein. For example, FIG. 2B illustrates an assembled plate 20 that includes a base 100 and an attached cover 300. The automated system as described herein refers to automated machinery (not shown) that includes machines to assemble the discrete strips 10 of bases 100, lids 200 and covers 300 to produce assembled plates 20 for testing and analysis. Such equipment also places media in the base 100 before the lid 200 is placed therein. In one example, the automated system performs heating and cooling functions to form assembled plates 20. Each base 100 is advanced through the system which adds or removes a lid 200 or a cover 300. The automated system may be any automated system known to those of ordinary skill in the art and may also include one adapted to recognize timing features for positive control of a continuous strip 10 of bases or assembled plates 20.

The bases 100 of the continuous strip 10 are interconnected via a weakened portion (not shown) along an edge of each adjacent base 100. In one example, a weakened portion can be a perforation at the point of delineation between bases 100, the perforation forming a line along interconnected edges of bases 100.

In the automated system and as shown in FIGS. 2A-2C, at various points during the assembly process, a continuous strip 10 in the automated system can include interconnected bases 100 only or it can include one or more assembled plates 20 such as bases 100 with a lid 200 (FIG. 2A), bases 100 with a cover 300 (FIG. 2B), or bases 100 with a lid 200 and a cover 300 (FIG. 2C). The components of the assembled plate depend on whether the assembled plate is in production, testing or analysis as it is advanced through the automated system.

The assembled plate 20 of the present invention can be used as a culture vessel used to culture microorganisms. Examples of microorganisms include viruses, bacteria, fungi, etc. The term sample or samples, as used throughout, is intended to refer generally to biological samples that contain microorganisms, such as the aforementioned examples.

The discrete portions of assembled plate 20 are made of materials selected to be compatible with the other portions of the plate assembly 20, as described further below.

As described herein and illustrated in FIGS. 3A-3D, the base 100, lid 200 and cover 300 include surfaces 110, 210 and 310. These surfaces are parallel to each other in the assembled plate 20. A direction generally perpendicular to the surface 110 of base 100 facing a source of agar injection or sample inoculation is referred to as an upward direction or where physical components of the assembled plate are referenced, a raised portion. The opposite direction, also generally perpendicular to the surface 110 of the base, is accordingly referred to as a downward direction with closed bottom surfaces to contain any materials used for testing.

The base 100 of the assembled plate 20 is sized to allow for placement onto and advancement through the automated system. The base 100 includes at least one top surface 110 and a reservoir 120 defined by a recessed surface remote from an at least one outer edge, e.g., 113, of the base 100. The reservoir 120 exists within outer walls 130 and has a volume sufficient to accommodate agar or culture media for inoculation with a sample to be tested. The terms agar and culture media as used herein both refer to media used for culture growth. The base 100 also includes physical attributes that provide positive control. The physical dimensions of the base 100 are not otherwise limited.

Figure 3A:
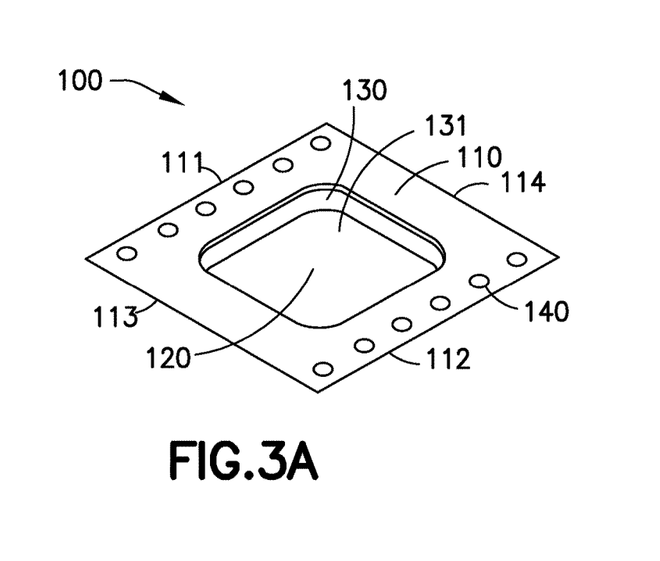
FIGS. 3A and 3B represent isometric and elevation views of a base of an assembled plate, respectively.
Figure 3B:
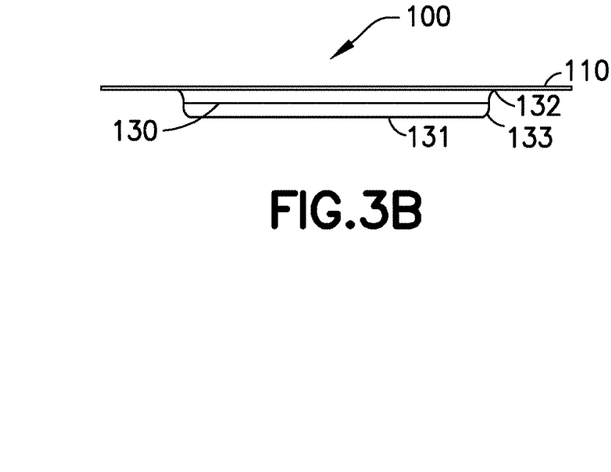

In one example, the base 100 is shown in FIGS. 3A and 3B. The base includes four edges 111, 112, 113, 114 defining a surface area. The surface area includes a top surface 110 separating the edges 111, 112, 113, 114 from a reservoir 120 remote from the edges of the base 100. The edges 111, 112, 113, 114 define a square or rectangular shape. The reservoir 120 of the base 100 is defined by side walls 130 and a bottom surface 131 as shown in FIG. 3A. The surface area of the bottom surface 131 of the reservoir 120 is less than the area defined by the perimeter of the base 100, the perimeter measured by the edges 111, 112, 113, 114. An intersection between the at least one side wall 130 and the lip 110 can be rounded 132 or at an angle. The intersection between the at least one side wall 130 and the bottom surface 131 can also be rounded 133 or at an angle. The volume within the reservoir 120 can be limited based on an allowable volume of agar. In one example where a conventional petri dish would otherwise be used, the size of the reservoir 120 is 3½ inches diameter by ⅝ inches depth. (100 mm×15 mm). The reservoir 120 can be configured to provide volumes similar to those typically used with petri dishes. Timing holes 140 can also be included on surface 110 to provide positive control of the speed at which the strip 10 is advanced through the system. As shown in FIG. 3A, the timing holes 140 are located on the lip 110 adjacent to two edges 111, 112 and are placed at equal spacing in a linear fashion so that a linear series of timing holes 140 is parallel to each of the edges 111, 112. Inclusion of the timing holes 140 also provides positive engagement for the continuous strip 10.

In another example, notches or other timing features (such as dimples, marks, print, etc.) can be used in place of holes to provide positive control.

In yet another example, the outer edge of the base 100 can define a circular or polygonal shape.

The base 100 is made of a material having barrier properties that prevent contamination of the culture/inoculated culture. Contamination is prevented for time periods that allow the media to be stored and the inoculated culture to be tested without significant contamination. A testing program can typically involve injection of an agar into the base, curing, inoculation with a sample, incubation and then analysis of the sample. The material properties of the base 100 should be such that the base 100 is sufficiently rigid at operating temperatures of the automated system to receive the lid 200. Thus, a base that is subject to warping at operating temperatures would not be suitable. The material from which the base 100 is made is sufficiently heat sensitive so that it can be molded at an elevated temperature typically used to mold articles. In addition, the material used for the base is generally transparent or translucent if the agar and sample are not light sensitive and is otherwise opaque. In view of the aforementioned guidance, the base 100 can be of any suitable material known to one of ordinary skill in the art.

Examples of material that can be used for the base 100 include conventional thermoplastic material. Examples of suitable thermoplastics include, but are not limited to, polyethylene terephthalate (PET) and polyvinyl chloride (PVC). A desired shape of the base 100 is formed by heating the thermoplastic material, molding it, and then allowing it to cool. Preferably, the base 100, lid 200 and cover 300 are made of the same material. In one example where the agar and sample are not light sensitive, the base 100, the lid 200 and the cover 300 are either translucent or transparent. In another example where the agar or sample are light sensitive, the base 100, the lid 200 and the cover 300 are opaque. In still further examples, the material for the assembled plate 20 can be chosen for its barrier properties based on the oxygen sensitivity of the agar and/or sample used in testing.

Labeling can also be added to individual bases or assembled plates. As described herein, labeling generally refers to a bar code, bull's eye code, ordinary text, text readable by software, or any other identifying mark. Labeling can be applied to a base 100 by any means known to those of ordinary skill in the art. An exemplary use of labeling applied to a bottom surface of a base involves association of that base with a corresponding sample. This allows ease of reference at a later juncture following incubation.

During production in one embodiment, the base 100 is assembled with a lid 200. The lid 200 is typically flat and has dimensions such that it at least substantially covers the lip 110 of the base 100. The flat surface of the lid 200 includes a top surface 210. The area of the top surface 210 can extend away beyond the perimeter of the base 100 measured on a plane. This allows for manual peeling of the lid 200 from the base 100.

Figure 3C:
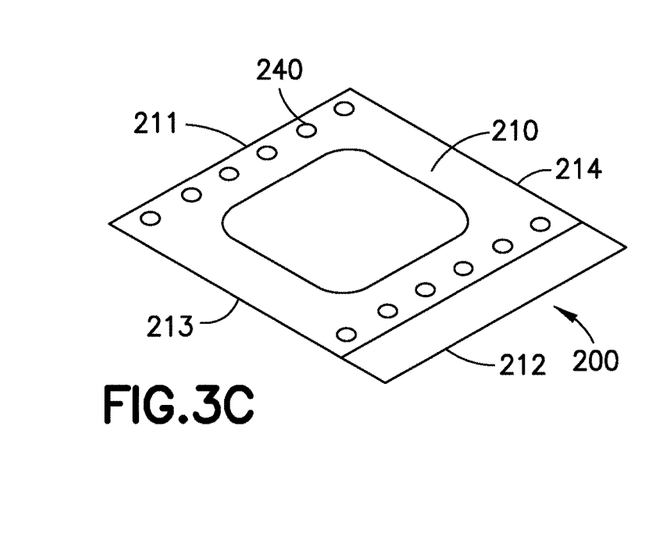
FIG. 3C represents an isometric view of a lid.

An example of the lid 200 is shown in FIG. 3C. In the example, the lid 200 includes a flat, planar top surface 210 with an outer boundary defined by four edges forming a rectangularly shaped perimeter. Two edges 211, 212 are equal in length to the edges 111, 112 of the base 100, while the other two 213, 214 are longer in one advantageous embodiment. In this example, timing holes 240 are sized and in locations matching those of the base 100 when the lid 200 is secured thereto. In this example, the length of the lid 200 is greater than the length of the base 100 in a direction parallel to the edges 213, 214.

Materials for the lid 200 can be the same types of materials as those used for the base 100. The material used for the lid 200, however, is not necessarily the same as the material used for the base 100. Rather, it derives from the same material criteria applicable to the base 100.

In one example, the lid 200 is formed with thermoplastic and is secured to base 100 by positioning the lid in a desired position relative to and in contact with the base and heating the lid 200 and the base 100 to bond them together. The assembled plate is then cooled by the system, causing the lid 200 to be sealed to the base 100 (hereinafter referred to as a "heat seal"). In other examples, the lid 200 is secured to the base 100 using other methods, such as via the use of a mechanical or an adhesive connection. A mechanical connection can be a hinged connection or a snap on connection whereby the lid 200 snaps into place over the base 100. Adhesives used can be any known to those of ordinary skill in the art.

At certain points of the testing and analysis process, and as shown in FIG. 2C, the assembled plate 20 further includes a cover 300. The cover 300, similar to the lid 200, is sized such that it at least completely covers the reservoir 120. The surface area of the cover 300 can also be larger in area than the area defined by the outer perimeter of the base 100.

Figure 3D:
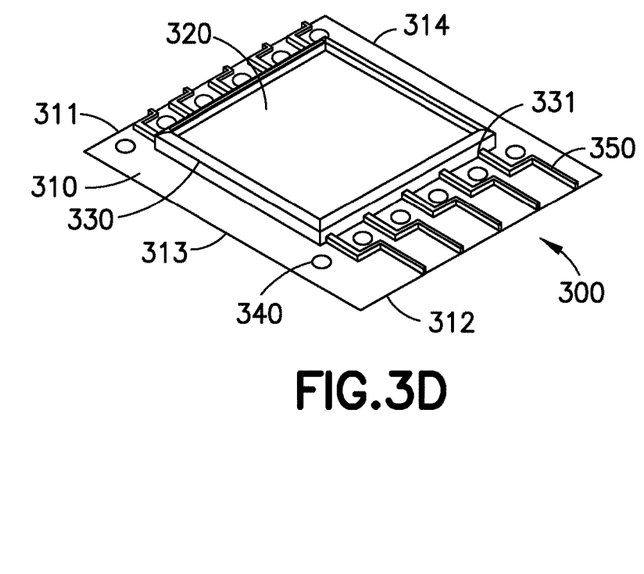
FIG. 3D represents an isometric view of a cover.

In an example of the first embodiment as shown in FIG. 3D, the cover 300 includes four edges forming an area with a rectangular shape, two of the edges 313, 314 longer than the other two edges 311, 312. The area defined by the edges 311, 312 of the cover 300 is larger than the area defined by the edges 111, 112, 113, 114 of the base 100, as shown in FIG. 3A. The side of the cover 300 extending to the edge 312 is longer than a corresponding side of the base 100, and allows the cover 300 to be peeled or otherwise separated from the base 100. The cover 300 includes a raised portion defined by side walls 330 extending from a surface 310 to an elevated surface 320, wherein the outer extent of the elevated surface 320 is defined by the top of side walls 330. When inoculated agar is in place in the reservoir 120 of the base 100 and the cover 300 is secured to the base 100, a volume of air exists within the raised portion of the cover 300. Prior to inoculation of the agar, the lid is removed. The agar is inoculated and the cover is placed over the base containing the inoculated agar. The assembly 20 is then incubated. During incubation there is no lid layer between the base and the cover.

The cover 300 is configured to provide an air gap above the agar. As shown in FIG. 3D, (in the embodiments where the base 100 includes timing holes 140), the cover also includes the timing holes 340 sized and located to correspond with timing holes 140 of the base 100. Also shown in FIG. 3D, the cover 300 includes one or more vents 350. Each vent extends through an opening 331 in the at least one side wall 330 and continues toward an edge 311, 312 of the cover 300. The trajectory of each vent along the cover surface 310 is illustrated as non-linear but can be linear. The non-linear vents 350 allow air flow from the inoculated agar and minimize contamination. Venting can also be achieved by the addition of gas permeable microbial barrier material. An example of a gas permeable microbial barrier is a Tyvek® patch manufactured by DuPont. The cover 300 can also use other filters known to those of skill in the art.

Materials for the cover 300 can be the same types of materials as those used for the base 100. The material used for the cover 300, however, is not necessarily the same as the material used for the base 100. Rather, it derives from the same material criteria applicable to the base 100. Thus, the material used for the cover 300 can be different than the material used for the base 100.

In one example, the cover 300 is formed with thermoplastic and is secured to the base 100 or the lid 200 by heating the cover 300, the base 100, and in some cases, the lid 200 to bond them together, then cooling the assembled plate 20, causing the cover 300 to be heat sealed to the base 100 and in some cases to the lid 200 as well. In other examples, the cover 300 is secured to the base 100 using other methods, such as the use of a mechanical or an adhesive connection. The mechanical connection can be a hinged connection or a snap-on connection whereby the cover 300 snaps into place over the base 100. Adhesives used can be any known to those of ordinary skill in the art.

Numerous benefits may be realized with the use of rollstock in conjunction with an automated system to form assembled plates 20 as described herein. One benefit when the components of the plate assembly 20 are thermoformed, allowing for securement of the base 100 with the lid 200 and the cover 300 via a heat seal, is the reduction in the amount of material needed to form a plate assembly. Thermoforming also typically uses less energy than injection molding. Another benefit is the ability to make plate assemblies smaller, and as a result there is less need for material to make the plate and less packaging for shipping and storing the plates. The efficacy of the rollstock plates described herein further reduces shipping costs due to a reduction in weight compared to standard petri dishes. The use of a thermoforming technique also allows for more flexibility in establishing a shape of the assembled plate 20. The specific shape of the assembled plate becomes largely a matter of design choice by the operator. The term operator, as used throughout, is intended to refer generally to the individual responsible for design and operation of the systems and methods described herein.

Yet another benefit of the present invention is that there is a lower risk of cross contamination between samples because the lid and cover are separate components. Once the lid is removed for inoculation, it is disposed of and the cover is placed over the inoculated agar. Sealing the bases to the lids also increases shelf life of the agar and allows for higher filling speed when implemented.

Other benefits of the invention are that the rollstock is less susceptible to damage during shipping. As noted above, the rollstock can be rollstock of individual plate components (i.e. base, lid or cover) or rollstock of assembled plates as shown in FIG. 2B (including bases and covers). Packaging and shipping the plate assemblies described herein is also simplified with the use of rollstock relative to conventional individual petri dishes systems.

Another benefit of the assembled plate 20 as disclosed herein is the reduction of secondary packaging (e.g., shrink wrap, boxes, and the like) commonly used with injection molded plates. Still another benefit is the ease of using the continuous rollstock strip 10, as shown in FIG. 1B, in an automated system. Ease of use is also enhanced because the roll configuration allows for easier loading into an automated system compared with prior art loose plates. Other benefits relating to methods of use are discussed below.

In another embodiment, an assembled plate 20 may comprise a base 100 and a lid 200 or a base 100 and a cover 300. However, in this embodiment, the assembled plate does not include a base, lid and cover simultaneously.

In yet another embodiment, the continuous strip 10 of bases 100 or assembled plates 20 described above is separated into individual bases 100 or assembled plates 20 prior to placement onto the automated system so that each may be processed individually. The continuous strip 10 may also be separated into a plurality of bases 100 or assembled plates 20.

In another embodiment, a continuous strip prepared for use in an automated system includes interconnected plate assemblies having bases and covers. In this embodiment, a separate continuous strip of lids can be provided.

In another aspect of the invention, a continuous strip 10, or rollstock, is supplied for use in a method of testing and analyzing samples. As described herein, the terms advance and forward are used to describe how the bases 100 or assembled plates 20 are moved during production, testing or analysis. In this way, the terms advance and forward are not limited in meaning to a particular physical direction of movement.

According to a first embodiment, a continuous strip 10 of interconnected bases 100 is supplied. The bases 100 include positive control to advance the bases in production. Positive control can be in the form of timing features. In one example, the bases 100 include timing holes 140. Timing holes align the continuous strip with the automated system. The spacing between timing holes is a matter of design choice and largely driven by the apparatus used to convey the strip through production. The timing holes permit the strip to be advanced through the system with consistent and controllable speed.

Initially, the rollstock or a portion thereof, as shown in FIG. 1B, is unwound for placement onto an automated system. This rollstock is designed for automation and is very easily adapted for placement onto an automated system.

Once unwound, the rollstock is loaded and aligned with the automated system using the timing holes of bases 100 so that a continuous strip 10 of bases 100 extends along a length of an initial segment of the automated system. In this configuration, the open face of the reservoir 120 of each base 100 of the continuous strip 10 is facing upward. This orientation allows an operator to inject agar or inoculate the agar with a sample as the base 100 is advanced by the automated system. See step 1 of FIG. 4. As the bases 100 advance, one or more individual bases 100 receive a culture media, also commonly referred to herein as agar, as shown in step 2 of FIG. 4. Typically, the agar is injected into the reservoir 120.

After receiving the agar, the base 100 advances through the automated system and a lid 200 is placed over the base containing agar. The lid may be an individual lid or it may be supplied from a continuous strip of lids and singulated or otherwise separated into a plurality of lids for placement onto the system. The lid 200 is then secured to base 100 in a manner that achieves an airtight seal, as described above and shown in step 3 of FIG. 4. As an example, such airtight seal may be achieved through forming a heat sealed connection between the base 100 and lid 200 where thermoplastic materials are used. When the lid 200 is placed in position, the automated system provides heat sufficient to ensure that the materials of the base 100 and the lid 200 bond together. As described above, a base 100 combined with another portion of an assembled plate, such as a lid or cover, is referred to herein as an assembled plate 20.

The automated system is arranged so that after the lid 200 is sealed to the base 100, each assembled plate 20 advances through the system and rotates into an inverted position so that it is upside down relative to its initial orientation. At this stage, the automated system proceeds to cool the advancing assembled plates, eliminating space between the lid 200 and the base 100, as shown in step 4 of FIG. 4. The agar cures in this orientation and in so doing an agar surface is produced that is flush with the lip 110 of the base 100. Because the lid is sealed onto the base in an airtight fashion there is substantially no air in the gap between the agar and the bottom surface of the reservoir. By employing a method using the materials and steps as described herein, an agar with a smooth surface is produced.

Once the agar is cured, the assembled plate 20 is inverted once again so that a surface of the lid 200 faces the upward direction. Lid 200 is then removed and disposed of and the agar is inspected for any irregular surface or any excessive moisture. See step 1-2 of FIG. 5. If the agar appears to be irregular in any way, does not have a surface flush with the lip 110 or has unacceptable moisture content, this indicates to the operator of the automated system that the assembled plate was improperly stored or that the heating and/or cooling process was defective. If the agar in the assembled plate has cured to the satisfaction of the operator, the assembled plate is separated from the continuous strip 10 behind it in the process. This is also known as "singulating" the assembled plates. Once the assembled plate is singulated, it is inoculated with a sample desired to be analyzed using methods known to those of ordinary skill in the art and as shown in step 3 of FIG. 5. Alternatively, the assembled plate can be singulated immediately following inoculation.

Following inoculation of the agar with the sample, a cover 300 is sealed to the base 100 so that the inoculated agar is not exposed to the environment. See step 4 of FIG. 5. As with the lids, the cover may be supplied as a singulated element or may be supplied from any portion of a continuous strip of covers. In one example, the cover 300 is formed from thermoplastic materials and, once placed over the base, can be heat sealed to the base 100. In another example, the cover can be affixed via a mechanical connection to the base 100, provided it is not exposed to the environment. At this stage, the assembled plate 20 can be set aside or left within the system to incubate for a desired period of time. See step 5 of FIG. 5.

Figure 5:
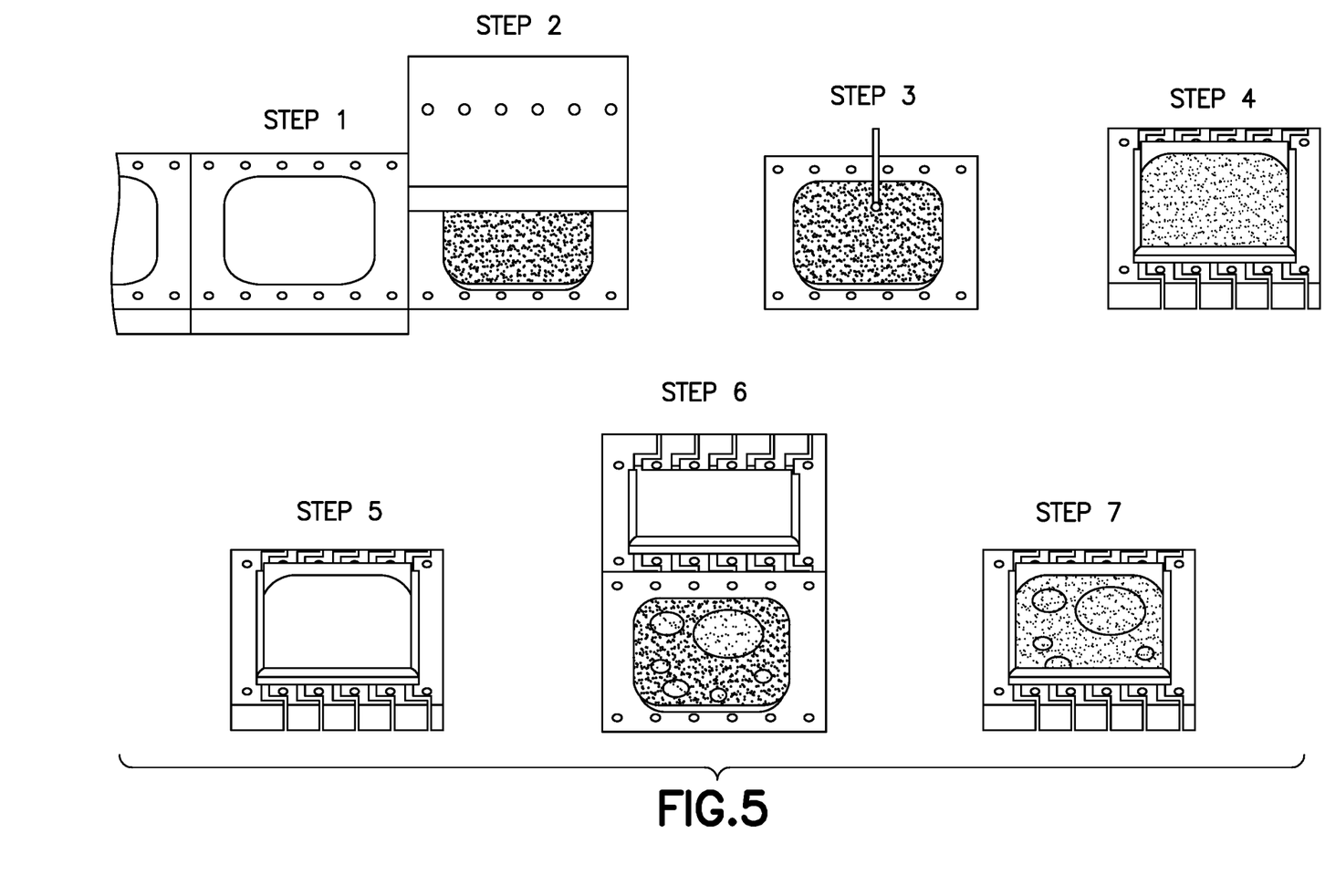
FIG. 5 represents a continuous strip of assembled plates and singulated plates as they would appear during the testing and analysis aspect of the method in one embodiment.

When the desired incubation period is complete, the cover 300 is lifted from the base 100 to allow inspection of the sample, as shown in step 6 of FIG. 5. This step may be repeated should it be determined that further incubation is required. See step 7 of FIG. 5.

Once inspection and analysis are completed, the cover 300 may once again be sealed or otherwise attached onto the used base 100 for disposal. In a variation, the cover 300 is disposed of after inspection and analysis are completed and a replacement disposal cover is attached onto the used base 100 instead of cover 300. The disposal cover is a separate element from cover 300 but otherwise includes the properties of cover 300 as described herein.

Numerous benefits may be realized via the methods of the present invention. One benefit is that the design is tailored for use with an automated system, particularly when the components of the assembled plate 20 include timing features. The use of a thermoforming process makes the inclusion of timing holes, notches, dimples, marks, print or other forms of positive control an attractive option in contrast to loose plate systems. Through the use of positive control, the processing of the continuous strip 10 within the automated system can be achieved with a greater level of predictability. Thus, the system achieves faster production of plate assemblies having an agar inoculated with a sample because there are fewer samples that must be discarded due to an inadequately cured agar or an improperly incubated sample. More broadly, positive control allows the automated system to operate at a higher rate of speed. Further benefits of positive control include a reduced need for separate molding, scheduling, storage and handling, thus reducing the labor needed to facilitate the process.

Another benefit is that the seal between the lid and the base is airtight and thus prevents contamination. Additionally, the gap between the lid 200 and the agar during curing of the agar is minimized and condensation forming between the agar and the lid is prevented. By inverting the assembled plates 20 after securing the lid 200 to the base 100 and cooling each assembled plate 20 with the agar therein, the automated system can cure the agar housed within each assembled plate with no gap between the lid 200 and the agar. At the same time, the method provides a means of determining whether the agar was improperly cured. For example, if the agar has an irregular surface, such as one with bumps or waves, it signals to the operator the possibility that the agar was subject to too much heat or cold, or that it was otherwise improperly stored during the curing process. If after removal of the lid 200 the agar appears moist, this also signals a defective agar. In addition to the above, this method of curing also provides for an increased shelf life of agar filled plate assemblies 20.

Yet another benefit is that rollstock is more compact, uses less material and takes up less space than a system using traditional injection molded and/or loose plates. Rollstock also has the ability to be stored even when bases 100 are filled with agar.

Another benefit is that environmental impacts are mitigated upon disposal when using cover 300 to form an airtight seal with bases 100 after use, as described above.

Finally, another benefit is the increased flexibility of preparing and analyzing samples achieved through the first embodiment of the method of this invention. The bases 100 or assembled plates 20 may be loaded onto the automated system as a continuous strip 10, but can also be loaded as individual bases 100 or assembled plates 20 and otherwise processed in the same way as described above. Alternatively, the above method can be performed manually without an automated system.

In another embodiment, the continuous strip 10 supplied includes assembled plates 20 that each have a base 100 and a cover 300 as described above. In one example, the base 100 can be as shown in FIGS. 3A and 3B and the cover 300 as shown in FIG. 3D. In further examples, each component is formed from thermoplastic material, and it is possible to secure the base 100 and the cover 300 to one another by heating the respective portions of the plate assembly to bond them, and subsequently cooling them to form a heat seal. In still other examples, mechanical connections may be used. Of course, all portions of the plate assembly are prepared prior to use as rollstock for an automated system. Separate from the continuous strip 10, lids 200 are added during the automated process. In one example, the lids 200 can be as shown in FIG. 3C. As described above, lids can be supplied from singulated lids or from any portion of a continuous strip of lids.

The plurality of assembled plates 20 that together form the continuous strip 10 are adapted for positive control when used in an automated system. In one example, each of the base 100, the lid 200 and the cover 300 include timing holes 140, 240, 340. The purpose and function of timing holes is as described above. As an example, the timing holes can provide positive control during the steps of initial loading of the continuous strip, injection of an agar, inoculation with a sample, incubation of an inoculated agar, and at all points in between. By having positive control, the operator of the system can be assured that each step of the method is reasonably predictable and is of a higher speed than prior art plated media systems.

The continuous strip of rollstock is unwound and is advanced into the automated system. The assembled plates are advanced through the system as described in the previous embodiment of the method described above until curing of the agar is completed. When curing of the agar is completed, the lids are disposed of.

Prior to inoculation of a sample in the agar, the assembled plates 20 of the continuous strip are singulated. The sample is then inoculated in the agar. The cover 300 attached to the base 100 is then closed so that the inoculated agar is not exposed to the environment, as described above. Where the steps of the previous embodiment of the method do not conflict with this embodiment, the steps of the previous method are hereby incorporated herein by reference.

In either of the above embodiments, step 6 as shown in FIG. 5 may be performed without removing the cover 300. In one example, the cover is not removed to inspect colony growth because the sample is sensitive or any exposure to the sample presents a danger. For example, fungal spores are inspected without removing the cover 300 due to the danger they present.

In another embodiment, the continuous strip is singulated after inoculation of a sample in the agar, but prior to incubation of the sample.

In any one of the above embodiments, the continuous strip as supplied can be separated into segments prior to use with the automated system. The continuous strip can include a plurality of bases or assembled plates, as applicable. For example, where rollstock includes a continuous strip of one hundred bases, the rollstock can be separated into two continuous strips of fifty bases each. Each of these strips can then be loaded into the automated system for injection with an agar and so on.

Figure 4:
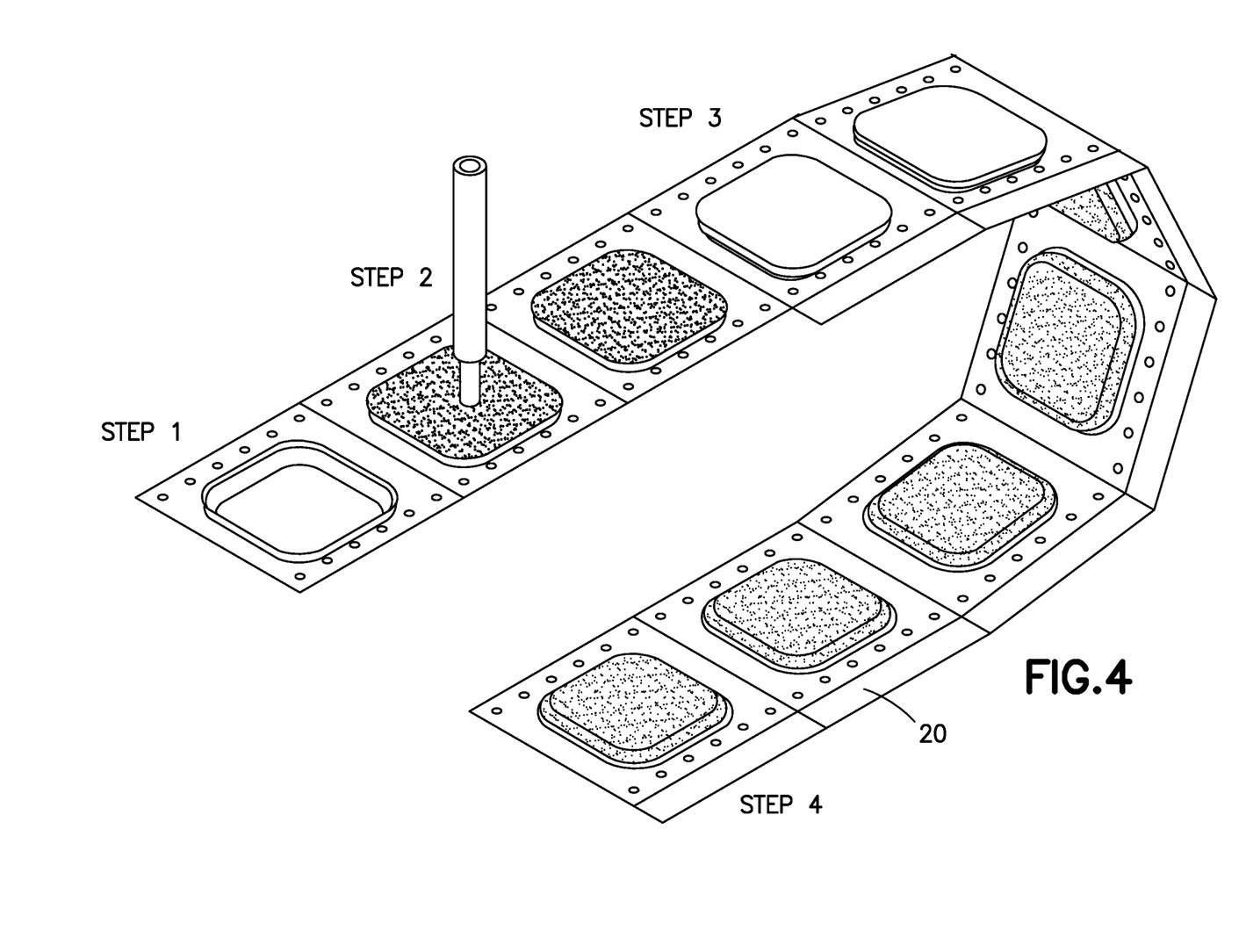
FIG. 4 represents a continuous strip of bases that are manufactured into plate assemblies as it would appear during the production step of the method in one embodiment.

In any one of the above embodiments, the method of testing and analysis can be performed manually, even though the method described herein is designed for automation. To perform the method manually, the continuous strip 10 having plates connected linearly in series is separated into individual bases 100 or assembled plates 20 prior to injection with an agar, i.e., prior to step 1 of the method as shown in FIG. 4. In the method according to this embodiment, the layers of the plate assembly may be provided without positive control. For example, bases can be supplied without timing features.

In any one of the above embodiments, the bases 100, lids 200 and covers 300 can be supplied without positive control. For example, if a manual testing procedure is adopted, the plate components can be provided without positive control.

In any of the above embodiments, labeling can be applied to one or more bases and/or assembled plates. Labeling can be applied to a base any time in the assembly process between initial manufacture of rollstock prior to distribution and the time of sample inoculation, or even later. Application of labeling may be via an adhesive, direct printing, or other known means. When labeling is applied to the base and/or assembled plate and includes identification in the form of a code, the labeling can be scanned using technology known in the art. In one example, the labeling contains a bar code that is scanned using a scanner. Scans or readings, where applicable, are typically performed at the time of inoculation to ensure the information on the label can be associated with the information related to the corresponding sample inoculated into the culture media. This system ensures that samples can be tracked through incubation and in subsequent analysis and storage stages as needed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of testing and analyzing samples using plated media, the method comprising:
    placing a first continuous strip of a plurality of interconnected bases adapted to provide positive control onto an automated system each base having a reservoir portion and a lip surrounding the reservoir;
    processing the first continuous strip of interconnected bases by depositing an agar in at least one of the bases;
    assembling the first continuous strip of bases to a second continuous strip of lids wherein each lid is adapted to be placed on and attached to the lip of each base;
    applying heat to bond the at least one base and the lid;
    advancing and inverting the plurality of interconnected bases and the lid;
    subjecting an inverted at least one base combined with lid thereon to reduced temperatures, under conditions selected to cure the agar;
    separating at least one base with a lid thereon from the plurality of interconnected bases with lids thereon, peeling and removing the lid from the at least one base, and inoculating the agar in the at least one base with a biological sample;
    securing a cover onto the at least one base;
    incubating the biological sample; and
    opening the cover to analyze the biological sample.

2. The method of claim 1 wherein the method further comprises:
    providing the plurality of interconnected bases in a roll;
    unwinding the roll so that the plurality of interconnected bases are ready for placement onto the automated system, wherein each base of the plurality of bases includes positive control features; and
    providing positive control when placing the plurality of interconnected bases onto the automated system to advance the bases through the system.

3. The method of claim 1, wherein the agar is cured while inverted for a time and at a temperature selected to provide a surface of the agar that is flush with the lid.

4. The method of claim 1, wherein the step of applying heat to bond the at least one base and the lid is at a temperature and for a duration that creates an airtight seal between the at least one base and the lid.

5. The method of claim 1, wherein securing a cover onto the at least one base further comprises applying heat to bond the cover and the at least one base.

6. The method of claim 1, further comprising resecuring the cover to the at least one base following analysis of the biological sample.

\* \* \* \* \*